United States Patent [19]

Gotou

[11] Patent Number: 5,445,812
[45] Date of Patent: Aug. 29, 1995

[54] ANGIOGRAPHIC ADJUVANT

[75] Inventor: Yasuyuki Gotou, Fuchu, Japan

[73] Assignees: The Green Cross Corporation; Taisho Pharmaceutical Co., Ltd., both of Japan

[21] Appl. No.: 325,648

[22] Filed: Oct. 19, 1994

Related U.S. Application Data

[63] Continuation of Ser. No. 547,076, Jul. 3, 1990, abandoned.

[30] Foreign Application Priority Data

Jul. 5, 1989 [JP] Japan ................................. 1-173709

[51] Int. Cl.$^6$ ..................... A01N 25/02; A01N 37/08; A61K 49/00; A61K 49/04
[52] U.S. Cl. ................................. 424/9.4; 514/573; 514/783; 514/786; 514/929; 514/974; 514/975; 424/9.1
[58] Field of Search .............. 514/573, 783, 786, 929, 514/974, 975; 424/9, 4

[56] References Cited

U.S. PATENT DOCUMENTS

| | | | |
|---|---|---|---|
| 4,493,847 | 1/1985 | Mizushima et al. | 514/573 |
| 4,820,732 | 4/1989 | Shell et al. | 514/573 |
| 4,880,634 | 11/1989 | Speiser | 514/786 |
| 4,955,878 | 9/1990 | See et al. | 514/573 |
| 5,064,636 | 11/1991 | Li et al. | 424/9 |
| 5,120,527 | 6/1992 | Li et al. | 424/9 |
| 5,124,352 | 6/1992 | Mizushima et al. | 514/510 |

FOREIGN PATENT DOCUMENTS

| | | |
|---|---|---|
| 0097481 | 6/1983 | European Pat. Off. . |
| 0132027 | 1/1985 | European Pat. Off. . |
| 0167825 | 6/1985 | European Pat. Off. . |
| 0150732 | 8/1985 | European Pat. Off. . |
| 0217419 | 10/1986 | European Pat. Off. . |
| 59-206349 | 11/1984 | Japan . |
| 59-216820 | 12/1984 | Japan . |

OTHER PUBLICATIONS

K. Korosue et al.; Clinical Effects of Lipo Prostaglandin E1 in Patients with Delayed Cerebral Vasospasm; STN File Server; (Kalsruhe) File Medline; Jun. 15, 1987, pp. 635–640.

Partial European Search Report, Application No. EP 90 30 7268.4 (1991).

*Primary Examiner*—Allen J. Robinson
*Assistant Examiner*—John D. Pak
*Attorney, Agent, or Firm*—Cushman Darby & Cushman

[57] ABSTRACT

An angiographic adjuvant comprising a fat emulsion containing a compound having prostaglandin E1 activities, and an angiographic method using the adjuvant.

8 Claims, No Drawings

ANGIOGRAPHIC ADJUVANT

This is a continuation of application Ser. No. 07/547,076, filed on Jul. 3, 1990, which was abandoned upon the filing hereof.

BACKGROUND OF THE INVENTION

1. Field of the Invention

This invention relates to a novel use of a fat emulsion containing a compound having prostaglandin $E_1$ activity. More particularly, it relates to an angiographic adjuvant, or an adjuvant used for promoting the blood flow in a region where angiography is to be performed, so as to make clear the angiographic pictures.

2. Related Art

Angiography is a clinical technique for observing the flow of a contrast medium such as an iodine compound injected into a blood vessel in a region by taking the pictures of such a flow of contrast medium through the vascular system in the region by X-ray photography, X-ray filming or other means. Angiography is used for diagnostical purposes such as (1) diagnosis on expansion or state of lesion in a blood vessel itself, (2) diagnosis of lesion, or its expansion, in various internal organs and their peripheral tissues from exclusive shadow or infiltrative shadow of the blood vessel, and (3) diagnosis on vascular movement or function by continuous photographing of the flow of contrast medium. For example, contrasting of superior mesenteric arteries is an important contrasting examination which is widely used for making decision on practicing arterial embolectomy for primary liver cancer, determination of the scope of infiltration of pancreatic cancer, diagnosis on esophageal varices, etc.

Hitherto, vasodilators such as prostaglandin $E_1$ (hereinafter referred to as $PGE_1$) injection and nitroglycerin injection have been used as angiographic adjuvant for making clear the pictures appearing on the screen or the photographs taken by angiography by increasing the blood flow in the region being examined when performing angiography.

The conventional angiographic adjuvants, however, were short in tolerable duration of sustained administration, making it hard to maintain their efficacy for a long time. It was also necessary to administer them at a high dose for performing long-time angiographical observation or for preventing embolus of fine blood vessels after angiography. Further, administration of said conventional adjuvants is accompanied with certain adverse side effects. For instance, it is reported that $PGE_1$ injection into superior mesenteric arteries may cause abnormal abdominal symptoms such as abdominal pain, burning sensation, tractional sensation, etc., and variation of blood pressure.

For eliminating these problems, an angiographic adjuvant capable of long-time retention in the system and showing a satisfactory efficacy at a small dose has been desired.

SUMMARY OF THE INVENTION

As a result of extensive studies to overcome the above problems of prior art, the present inventors accomplished the present invention which is predicated upon the discovery that use of a fat emulsion containing a compound having $PGE_1$ activities as an angiographic adjuvant in performing angiography can improve the efficacy retention time and also has the effect of enabling a decrease of dose and reduced manifestation of side effects in the administered region.

Thus, the angiographic adjuvant of this invention made for solving said prior art problems is characterized by comprising a fat emulsion containing a compound having $PGE_1$ activities.

The present invention is also intended to provide an angiographic method comprising administering to man a fat emulsion containing a compound having $PGE_1$ activities.

DESCRIPTION OF THE PREFERRED EMBODIMENTS

The compounds having $PGE_1$ activities usable in the present invention are not subject to any particular restrictions provided that they are pharmaceutically acceptable ones and have $PGE_1$ activities. Typical examples of such compounds are $PGE_1$ and its derivatives.

The $PGE_1$ derivatives usable as said compound in this invention may be of any type as far as they have $PGE_1$ activities and are suited for adaptation as a pharmaceutical agent. Preferred examples of such $PGE_1$ derivatives are shown, for example, in Japanese Patent Application Laid-Open No. 206349/84 (EP-A-132027) and No. 216820/84.

A preferred example of fat emulsion containing a compound having $PGE_1$ activities, which constitutes active ingredient of the angiographic adjuvant according to this invention, comprises, as main constituents, 5–50% (W/V) of a vegetable oil (such as soybean oil, sesame oil, castor oil, cottonseed oil, olive oil and the like, among which soybean oil is preferred), 1–50, preferably 5–30 parts by weight of phospholipid for 100 parts by weight of vegetable oil, a proper quantity of water, and a compound having $PGE_1$ activities. In addition, the fat emulsion may contain, if necessary, an emulsifying adjuvant (for example, up to 0.3% (W/V) of a fatty acid having 6–22, preferably 12–20 carbon atoms or a pharmaceutically acceptable salt thereof), a stabilizer (for example, 0.5% (W/V), preferably 0.1% (W/V) or less of a cholesterol or 5% (W/V), preferably 1% (W/V) or less of phosphatidic acid), a polymeric substance (for example, 0.1–5, preferably 0.5–1 part by weight of albumin, dextran, vinyl polymer, nonionic surfactant, gelatin, hydroxyethyl starch or the like for 1 part by weight of said compound having $PGE_1$ activities (such as $PGE_1$ or its derivatives), and an isotonizing agent (for example, glycerin or glucose). The content of the compound having $PGE_1$ activities in said fat emulsion can be suitably varied according to the formulation of the emulsion, way of administration and other factors, but it should cover the effective amount which is in the range of 0.2 to 100 μg/ml.

The vegetable oil for use in the present emulsion is preferably a highly purified soybean oil, more preferably the one (purity: 99.9% or above in terms of total glyceride including tri-, di- and monoglyceride) obtained by further purifying common refined soybean oil by steam distillation.

The phospholipid used in the present emulsion composition is a purified phospholipid such as egg yolk lecithin or soybean lecithin, which can be obtained by the common fractionation using an organic solvent. The desired purified phospholipid can be obtained, for example, by slowly adding, with stirring, acetone to a crude yolk phospholipid dissolved in an cold n-hexaneacetone mixture, collecting the insolubles by filtration, repeating the above operation once more, and removing the solvent by distillation. The product comprises phosphatidylcholine and phosphatidylethanolamine as major costituents and minor amounts of other phospholipids such as phosphatididylinositol, phosphatidylserine and sphingomyelin.

One may use a phospholipid containing substantially no phosphatidylcholine which, is prepared by purifying further, purified phospholipid according to the method disclosed in U.S. Pat. No. 4684633 (EP-A-150732).

The fatty acids of 6–22 carbon atoms for use as emulsifying adjuvant are those suitable for use in pharmaceuticals. They may be of ether straight chain or branched chain. Most preferred are straight chain fatty acids such as stearic, oleic, linolic, palmitic, linoleic, and myristic acids. The salts of these acids should be physiologically acceptable ones such as, for example, alkali metal salts (sodium salt, potassium salt, etc.) and alkaline earth metal salts (calcium salt, etc.).

The cholesterols or phosphatidic acids usable as stabilizer in the present emulsion composition may be of any known types which are capable of pharmaceutical usage.

Suitable polymeric substances for use in the emulsion of this invention are as follows. The albumin should be of the human origin, in view of the problem of antigenicity. Suitable vinyl polymers include polyvinylpyrrolidone.

Suitable nonionic surfactants are polyalkylene glycols (for example, polyethylene glycol having an average molecular weight of 1,000–10,000, preferably 4,000–6,000), polyoxyalkylene copolymers (for example, Polyoxyethylene-polyoxypropylene copolymer having an average molecular weight of 1,000–20,000, preferably 6,000–10,000), polyoxyalkylene derivatives of hardened castor oil (for example, hardened castor oil polyoxyethylene-(40)-, or -(20) or -(100) ether), and polyoxyalkylene derivatives of castor oil (for example, castor oil polyoxyethylene-(20), -(40) or -(100) ether).

Glycerin and glucose used as isotonizing agent in the present emulsion may be of any origin as far as they are pharmaceutically usable ones.

The fat emulsion used in the present invention can be prepared in the various ways, a typical example of which is as follows. Predetermined amounts of a vegetable oil (preferably soybean oil), phospholipid, a compound having $PGE_1$ activities and, if necessary, the afore-mentioned additives are mixed and heated to form a solution. This solution is homogenized by a commonly used type of homogenizer (such as high pressure-jet type or ultra- sonic type homogenizer) to prepare a water-inoil type dispersion. This dispersion is added with a necessary amount of water and again homogenized by said homogenizer to convert said dispersion into an oil-in-water type emulsion, whereby a desired fat emulsion can be obtained. The thus produced fat emulsion may be further added with additives such as stabilizer, isotonizing agent, etc., if necessary for the reasons relating to the preparation process (U.S. Reg. No. 4493847, EP-A-97481).

The angiographic adjuvant of this invention comprising said fat emulsion is usually administered intravenously or intraarterially, or through other suitable routes. Usually said adjuvant is administered at a dose of about 1 to 50 μg in terms of active principle, but the dose is variable depending upon the condition of the patient, the region to be examined and other matters.

The angiographic adjuvant of this invention can be used for performing various modes of angiography, including both arteriography and venography. For example, the angiographic adjuvant of this invention can be used for superior mesenteric arteriography, carotid arteriography, abdominal arteriography, femoral arteriography, pulmonary venography and interior aortography.

ADVANTAGEOUS EFFECT OF THE INVENTION

The angiographic adjuvant according to the present invention is capable of long-time retention of its efficacy in the living bodies and exhibits the desired action with a small dose. This may be attributed to the following reasoning. Usually $PGE_1$ is rapidly inactivated upon combining with albumin in the living body, so that when using $PGE_1$ as an angiographic adjuvant, it is hard to maintain its efficacy for a long time, but in the case of the angiographic adjuvant according to this invention, the adjuvant compound having $PGE_1$ activities is formulated into a fat emulsion and can be absorbed into the blood vessel through its endothelium in a very stable state, so that it can retain its efficacy for a long time with a small dose.

As described above, the angiographic adjuvant of this invention has the advantage of enabling a decrease of dose, which results in reduced side effects, and also contributes to the prevention of embolus of fine blood vessels after the angiographic operation. Thus, the preparation of this invention is very useful for its clinical use as an adjuvant in the practice of angiography.

EXAMPLES

The present invention is illustrated below in detail with reference to Examples and Test Examples of the preparation according to this invention, but these examples are merely intended to be illustrative and not to be construed as limiting the scope of the invention.

EXAMPLE 1

To 30 g of purified soybean oil were added 3.6 g of yolk phospholipid, 900 μg of $PGE_1$, 0.15 g of sodium palmitate and 0.15 g of phosphatidic acid. The mixture was heated at 40° to 75° C. to form a solution. To the solution was added 200 ml of distilled water, followed by the addition of 7.5 g of glycerin of the official grade (Pharmacopoeia of Japan). The mixture was made up to 300 ml with distilled water for injection at 20° to 40° C. and coarsely emulsified by a homomixer.

The coarse emulsion was homogenized by passing it 10 times through a Manton-Gaulin type homogenizer under a first-stage pressure of 120 kg/cm$^2$ and a total pressure of 500 kg/cm$^2$. There was obtained a homogenized, finely dispersed fat emulsion containing $PGE_1$ (This preparation is hereinafter referred to as $PGE_1$-lipo). The emulsion, 0.2–0.4 μ in average size of dispersed droplets, contained none of the droplets of 1 μ or above in size.

EXAMPLE 2

A fat emulsion was prepared following the same recipe and the same procedure as in Example 1, except that 0.15 g of sodium oleate was used in place of 0.15 g of sodium palmitate and 0.15 g of phosphatidic acid.

TEST EXAMPLES

The effect of the angiographic adjuvant of this invention was tested by superior mesenteric portal venography and measuring the change in blood flow rate through the portal vein.

I. Test method (1) Subjects

Selected as test subjects were 10 cases (7 men and 3 women, 44–68 in age, average age: 64.4) who have been subjected to abdominal angiography. Diagnoses at the time of practice of angiography confirmed 4 cases of primary liver cancer, 2 cases of metastatic liver cancer, 2 cases of cirrhosis of the liver and 2 cases of pancreas cancer.

(2) Abdominal angiography

After puncturing a femoral artery of each subject, a sheath was inserted into said artery by Seldinger method. Then a catheter for angiography (cobra-shaped, RH Type 5.5F, mfd. by Cook Corp.) in said sheath was passed into the main superior mesenteric artery and a contrast medium (Iopamidol; iodine concentration: 370 mg/1) was injected at a rate of 5 ml/sec for 10 seconds (for a total amount of 50 ml). Pictures were taken on 16 films during a period of 30 seconds after start of injection. Thereafter, an α-cyclodextrin clathrate compound of $PGE_1$ (hereinafter referred to as $PGE_1$-CD) or $PGE_1$-lipo was intraarterially injected into said superior mesenteric artery at a dose of 20 μg in terms of $PGE_1$ in the case of $PGE_1$-CD and 10 μg in terms of $PGE_1$ in the case of $PGE_1$-lipo, immediately followed by angiographic observation and photographing.

Portal venographical pictures were taken and the change of blood flow rate was measured for the 5 cases to which $PGE_1$-CD was intraarterially injected after intraarterial injection of contrast medium alone (these cases are hereinafter referred to as case group I) and for another 5 cases to which $PGE_1$-lipo was intraarterially injected after intraarterial injection of contrast medium alone (these cases are hereinafter referred to as case group II), and these two case groups were subjected to a comparative examination in connection to the following test items.

(3) Test items and test method (i) Measurement of contrast medium concentration

As an index of concentration of contrast medium in the blood vessel, measurement was made of concentration for the contrasted blood vessels on the films by a Fuji Densitometer 301. Measurement was made at the following three regions: main superior mesenteric vein, main portal vein and right branch of portal vein. The average of the measured values at said three regions was given as the determined value.

(ii) Measurement of blood vessel diameter

The blood vessel diameter in the main portal vein was measured on the contrastradiographic films before and after arterial injection of $PGE_1$-CD or $PGE_1$-lipo.

(iii) Measurement of change of branch

Change in improvement of fixing of branch by use of $PGE_1$-CD or $PGE_1$-lipo in portal venography was examined. Branches on the films were identified in case group I and case group II, and the changes before and after arterial injection of $PGE_1$-CD or $PGE_1$-lipo were compared.

(iv) Measurement of change of blood flow rate in portal vein

Change of blood flow rate in portal vein was measured by ultrasonic pulse Doppler method. $PGE_1$-CD or $PGE_1$-lipo was arterially injected into the portal vein from the superior mesentric artery, and the blood flow rate in the main portal vein was measured by ultrasonic pulse Doppler method (using a device SSD-650 mfd. by Aloca Co., Ltd.). The blood flow rate was calculated from the measured average flow velocity and the sectional area of the main portal vein determined from the B mode image.

II. Test results (1) Measurement of contrast medium concentration

The concentrations at the three regions: main superior mesentric vein, main portal vein and right branch of portal vein on the contrastradigraphic films were statistically aggregated. From a comparison of the portal venographical images after arterial injection of $PGE_1$-CD or $PGE_1$-lipo with those observed when using contrast medium alone, an increase of contrast medium concentration to a significant degree was noted for both $PGE_1$-CD and $PGE_1$-lipo, but there was seen no statistically significant difference between $PGE_1$-CD and $PGE_1$-lipo at the doses used in this test ($P<0.01$). In view of the $PGE_1$ dose of 20 μg in case of administering $PGE_1$-CD and 10 μg in case of administering $PGE_1$-lipo, it was found that $PGE_1$-lipo can produce the same effect as $PGE_1$-CD with half the amount of active principle of the latter.

(2) Measurement of blood vessel diameter

The changes of blood vessel diameter in main portal vein were as shown in Table 1 (case group I) and Table 2 (case group II). In both of case groups I and II, a significant expansion of blood vessel diameter by arterial injection of $PGE_1$-CD or $PGE_1$-lipo was observed. However, there was seen no statistically significant difference between $PGE_1$-CD and $PGE_1$-lipo at the doses used in the present test. This attests to the fact that $PGE_1$-lipo can produce the same effect as $PGE_1$-CD by administering half the amount of $PGE_1$-CD in terms of quantity of active principle.

TABLE 1

| | (case group I) | |
|---|---|---|
| | Blood vessel diameter (mm) | |
| Case No. | When contrast medium alone was used | After arterial injection of $PGE_1$-CD |
| 1 | 12 | 16 |
| 2 | 16 | 18 |
| 3 | 17 | 19 |
| 4 | 15 | 17 |
| 5 | 12 | 15 |

TABLE 2

| | (case group II) | |
|---|---|---|
| | Blood vessel diameter (mm) | |
| Case No. | When contrast medium alone was used | After arterial injection of $PGE_1$-lipo |
| 1 | 10 | 14 |
| 2 | 12 | 16 |
| 3 | 12 | 16 |
| 4 | 14 | 17 |
| 5 | 14 | 15 |

(3) Measurement of change in branches

The results of identification of branches in the intrahepatic portal vein by observation of portal venographic pictures were as follows. In the case of case group I, when contrast medium alone was arterially injected, there was 2 cases in which 3 branches could be identified and 3 cases in which 4 branches could be identified. On the other hand, when $PGE_1$-CD was arterially injection, 4 branches could be identified in all cases and as much as 5 branches could be identified in 2 cases. No change was seen in one case. There was noted an improvement in 4 out of 5 cases.

In the case of case group II, when contrast medium alone was injected, 4 branches could be identified in all 5 cases, and when $PGE_1$-lipo was used, 5 branches could be identified in 4 cases. An improvement was seen in 4 out of 5 cases. The above results suggest that $PGE_1$-CD and $PGE_1$-lipo have the same effect regarding identification of fine intrahepatic portal vein vessels at the dose used in the present test, and this was consistent with the static analyses. It was thus ascertained that $PGE_1$-lipo can produce the same effect as $PGE_1$-CD with half the amount of active principle of the latter.

(4) Determination of change in blood flow rate in portal vein

The change of blood flow rate in portal vein was determined by ultrasonic pulse Doppler method, obtaining the results shown below.

In case group I, the blood flow rate in portal vein before arterial injection of $PGE_1$-CD was $9.5 \pm 3.0 \times 10^2$ ml/min, but one minute after arterial injection of $PGE_1$-CD, said blood flow rate increased to $16.9 \pm 6.8 \times 10^2$ ml/min. On the other hand, in case group II, the blood flow rate in portal vein before arterial injection of $PGE_1$-lipo was $8.4 \pm 3.1 \times 10^2$ ml/min, but one minute after arterial injection of $PGE_1$-lipo, it showed a significant increase to $14.8 \pm 4.3 \times 10^2$ ml/min. This was quite significant in statistical terms, too. Also, it is considered that both $PGE_1$-CD and $PGE_1$-lipo have the equal effect at the doses used in the present test, and it was found that $PGE_1$-lipo can produce the same effect as $PGE_1$-CD with half the content of active principle of the latter.

(5) Side effects

In superior mesentric arterial injection of $PGE_1$, certain undesirable abdominal symptoms such as abdominal pain, burning sensation, tractional sensation, etc., and other adverse side effects such as variation of blood pressure have been reported in the past. However, in the 5 cases to which $PGE_1$-lipo has been injected in the present test, there was none which complained of said abdominal symptoms and also there took place no variation of blood pressure exceeding 20 mmHg.

What is claimed is:

1. A human angiographic method employing the following steps:
   administering, intravenously or intraarterially an angiographic effective amount of an angiographic adjuvant including a fat emulsion and a principal active agent being PGE;
   observing a flow of angiographic contrast medium.

2. The angiographic method of claim 1 wherein said angiographic adjuvant is administered at a dose of about 1 to 50 µg in terms of the active principal agent.

3. The angiographic method of claim 1 wherein said method is employed for arteriography and venography.

4. The angiographic method of claim 1 wherein said method is employed for performing superior mesenteric arteriography, carotid arteriography, abdominal arteriography, femoral arteriography, pulmonary venography and interior aortography.

5. The angiographic method of claim 1 wherein said fat emulsion includes vegetable oil, phospholipid and water.

6. The angiographic method of claim 1 wherein said fat emulsion includes an additive selected from the group consisting of emulsifying adjuvant, stabilizer, polymer, and isotonizing agent.

7. The angiographic method of claim 1 wherein the administration of said angiographic adjuvant increases blood vessel diameter by 7–40%.

8. The angiographic method of claim 1 wherein the administration of said angiographic adjuvant increases blood flow rate by 66–98%.

* * * * *